US009289534B2

(12) United States Patent
Lehtonen et al.

(10) Patent No.: US 9,289,534 B2
(45) Date of Patent: Mar. 22, 2016

(54) BIOCOMPATIBLE COMPOSITE AND ITS USE

(75) Inventors: Timo Lehtonen, Turku (FI); Jukka Tuominen, Kaarina (FI)

(73) Assignee: Purac Biochem bv, AC Gorinchem (NL)

(*) Notice: Subject to any disclaimer, the term of this patent is extended or adjusted under 35 U.S.C. 154(b) by 116 days.

(21) Appl. No.: 13/265,823

(22) PCT Filed: Apr. 22, 2010

(86) PCT No.: PCT/EP2010/055335
§ 371 (c)(1),
(2), (4) Date: Oct. 21, 2011

(87) PCT Pub. No.: WO2010/122098
PCT Pub. Date: Oct. 28, 2010

(65) Prior Publication Data
US 2012/0040015 A1 Feb. 16, 2012

(30) Foreign Application Priority Data
Apr. 23, 2009 (EP) .................................. 091585976

(51) Int. Cl.
*A61L 29/12* (2006.01)
*A61L 27/44* (2006.01)
*A61L 31/12* (2006.01)

(52) U.S. Cl.
CPC .............. *A61L 29/126* (2013.01); *A61L 27/446* (2013.01); *A61L 31/128* (2013.01)

(58) Field of Classification Search
None
See application file for complete search history.

(56) References Cited

U.S. PATENT DOCUMENTS

| 5,108,957 A | 4/1992 | Cohen et al. | 501/35 |
| 5,914,356 A * | 6/1999 | Erbe | 523/114 |
| 6,399,693 B1 | 6/2002 | Brennan et al. | 524/494 |
| 2005/0008620 A1 | 1/2005 | Shimp et al. | 424/93.7 |
| 2005/0142077 A1 | 6/2005 | Zimmer et al. | 424/57 |
| 2006/0020266 A1 | 1/2006 | Cooper | 606/77 |
| 2007/0003625 A1* | 1/2007 | Seo et al. | 424/486 |
| 2007/0015685 A1* | 1/2007 | Balaban | 514/2 |

FOREIGN PATENT DOCUMENTS

| EP | 0 412 878 | 2/1991 |
| EP | 1 048 625 | 11/2000 |
| EP | 1 665 042 | 5/2006 |
| FR | 2 658 182 | 8/1991 |
| FR | 2 781 788 | 2/2002 |
| WO | WO 94/14401 | 7/1994 |
| WO | WO 96/21628 | 7/1996 |
| WO | WO 98/46164 | 10/1998 |

OTHER PUBLICATIONS

Glass, (Feb. 5, 2009), pp. 1-17.*
Boccaccini, A.R., Journal of Materials Science: Materials in medicine, 14 (2003) pp. 443-450.*
Liu, Aixue, et al., Acta Biomaterialia, 4 (2008) pp. 1005-1015.*
Pirhonen, Eija, et al., Key Engineering Materials vol. 192-195 (2001), pp. 725-728.*
Kellomaki et al., "Bioabsorbable scaffolds for guided bone regeneration and generation," 21 *Biomaterials* 2495 (2000).

* cited by examiner

*Primary Examiner* — Brian-Yong Kwon
*Assistant Examiner* — Lyndsey Beckhardt
(74) *Attorney, Agent, or Firm* — James C. Lydon

(57) ABSTRACT

A composite material including biocompatible and bioresorbable glass, a biocompatible and bioresorbable matrix polymer and a coupling agent capable of forming covalent bonds. The composite also includes a compatibilizer, where at least 10% of the structural units of the compatibilizer are identical to the structural units of the matrix polymer, and the molecular weight of the compatibilizer is less than 30000 g/mol. The use of this composite, a medical device which includes the composite and a method for preparing the composite are also disclosed.

17 Claims, 1 Drawing Sheet

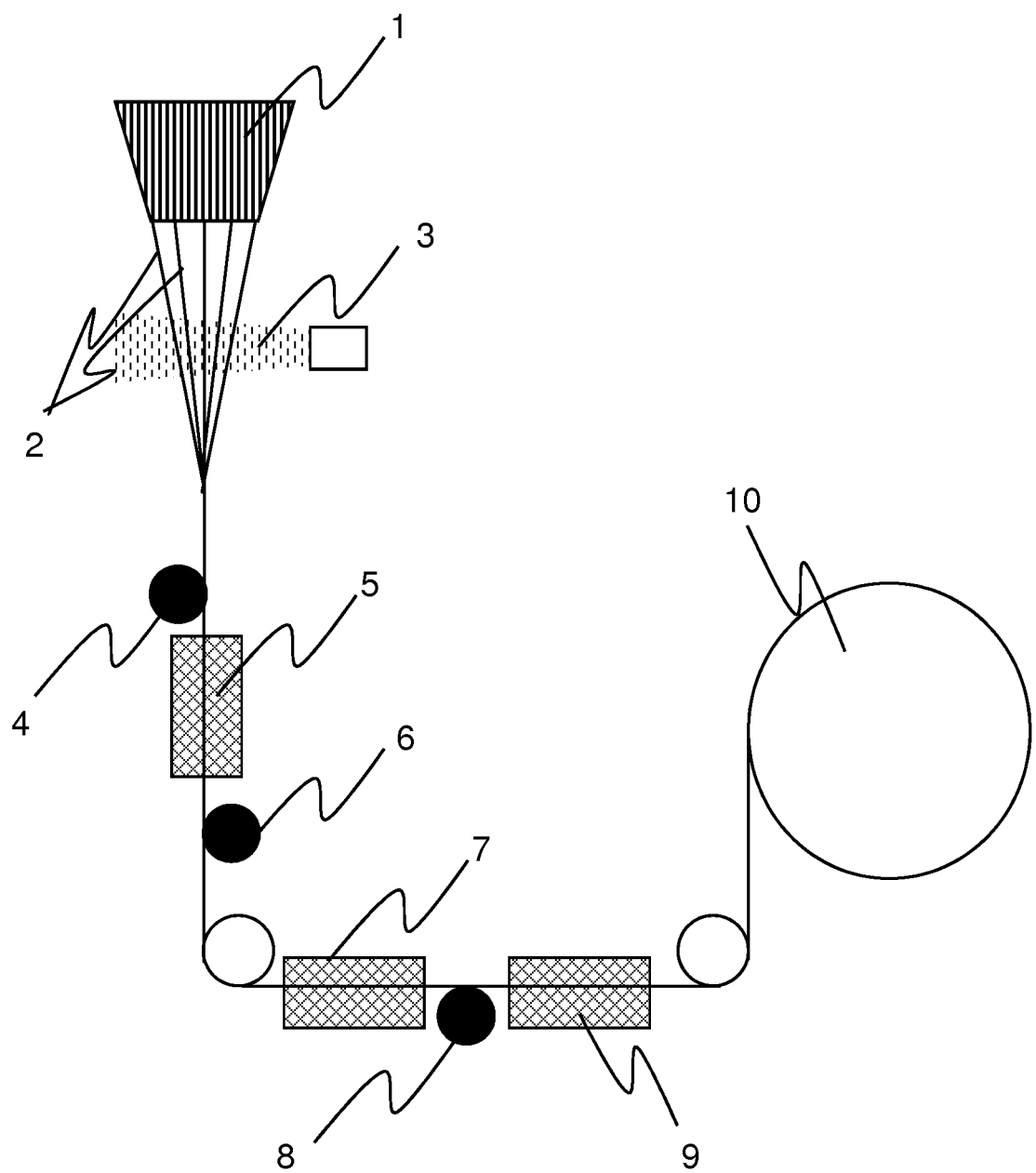

BIOCOMPATIBLE COMPOSITE AND ITS USE

The invention relates to a composite material comprising biocompatible and bioresorbable glass, a biocompatible and bioresorbable matrix polymer and a coupling agent capable of forming covalent bonds. The invention further relates to the use of this composite material as well as to devices comprising said composite material. The invention also relates to a process for manufacturing a composite material according to this invention.

BACKGROUND OF THE INVENTION

Medical implants can be manufactured from alloys, ceramics or both degradable and stable composites. The choice of implant material selection is always a combination of material property requirements, the type of fixation needed, knowledge and skills of the physician, patient's needs and expectations and sometimes a compromise has to be done between available materials and the requirements of the healing process and the quality of life after trauma, fixation etc. In general, the lack of suitable materials in the market restricts the development and design of certain types of implantable devices.

Traditionally alloys have been used to make bone pins, screws and plates and indeed, for certain applications they still are well suited for carrying external load. However, bone resorption may often be seen due to the strength and stiffness of the alloy compared with the bone. In addition to this hardness problem, another disadvantage is the lack of material degradability in vivo. In order to avoid the bone resorption after the healing process, a second surgery is required to remove the implant, which always causes an additional risk and added morbidity for the patient, occupies the availability of clinic and increases the overall costs (Bradley et. al. Effects of flexural rigidity of plates on bone healing. J Bone Joint Surg 1979; 61A:866-72.).

Biostable polymers and their composites e.g. based on polymethacrylate, ultra high molecular weight polyethylene (UHMWPE), polytetrafluoroethylene (PTFE), polyetheretherketone (PEEK), polysiloxane and acrylic polymers are known in the literature (S. Dumitriu, Polymeric Biomaterials $2^{nd}$ ed., CRC Press, 2001), and polymer composites have been used to manufacture medical implants. However, they are neither bioactive nor resorbable and thus will not be replaced by natural bone. Although being weaker than the alloy implants they still suffer similar problems than alloys and may require a second surgery for replacing or removing the implant at some point of the lifetime of the implant.

The biological and mechanical properties of bone result from its microstructural features. Bone is a composite material made up of organic and inorganic components, where the inorganic or mineral phase represents 60-70% of the total dry bone weight. The organic phase is a viscous gel-like material comprised primarily of collagen while the mineral component consists of a crystalline form of calcium phosphate containing carbonate ions, small amounts of sodium, magnesium, hydrogenophosphate ions and other trace elements.

Various bioactive glass compositions are known in the field. They are able to bond to bone and soft tissue, and they may be used for stimulating tissue or bone growth in a mammalian body. Bioactive glass also typically guides the formation of new tissue, which grows within said glass. When bioactive glasses come into contact with a physiological environment, a layer of silica gel is formed on the surface of the glass. Following this reaction, calcium phosphate is deposited to this layer and finally crystallized to a hydroxyl-carbonate apatite. Due to this hydroxyl-carbonate apatite layer the resorption of the bioactive glass is slowed down when inserted into a mammalian body. For decades, bioactive glasses have been investigated as bone filling materials that can bond with bone, even chemically. Recent discoveries of the superior qualities of bioactive glasses have made the materials far more interesting for these applications. Certain bioactive glasses have been commercially sold under the trade names of e.g. BonAlive®, Novabonea and Biogran®. Bioactive glasses have been used in different forms for medical applications, such as granules and plates for orthopaedic and cranio-maxillofacial bone cavity filling and bone reconstruction. Certain bioactive glass formulations have been disclosed in the prior art, e.g. publications EP 802 890 and EP 1 405 647. Some compositions of bioactive glasses are known to have antimicrobial effects, see for example publications U.S. Pat. No. 6,190,643 and U.S. Pat. No. 6,342,207.

Other types of resorbable glass compositions are also known in the field. Resorbable glasses are not necessarily bioactive, i.e. they do not form a hydroxyl-carbonate apatite layer on the glass surface. Resorbable glass compositions are used in the glass fiber industry to resolve the problem of glass fibers ending up e.g. in lungs during installation of glass fiber insulation. Disappearance of the fibers is preferably relatively fast, so that no detrimental effects are caused to the body. One resorbable glass composition is disclosed in document EP 412 878. The fibers are degraded under 32 days. Such degradation rate is, however, too fast for most medical applications, for example for screws or pins for fixing bone defects or fractures.

Documents EP 915 812 and EP 1 484 292 disclose biosoluble glass composition to improve occupational health and safety. Document WO 03/018496 discloses anti-inflammatory, wound-healing glass powder compositions. Publication U.S. Pat. No. 6,482,444 discloses silver-containing bioactive sol-gel derived glass compositions to be used in implanted materials, for preparation of devices used for in vitro and ex vivo cell culture.

Document EP 802 890 discloses a bioactive glass composition with a large working range. Devitrification problems are circumvented by adding potassium and optionally magnesium to the glass.

One aspect of the fiber glass composition is to prevent neuro and/or cytotoxic effects derived from the fiber glass compositions containing potassium and/or a high local pH raise due to a too fast degradation rate of glass fibers.

Although bioactive glass and glass fibers are being well accepted by the body and have proven to be excellent biomaterials for bone fixation applications, bioactive glass lacks the required mechanical properties for load bearing applications. Indeed, bioactive glass is a hard and brittle material.

Resorbable polymers have been used to develop resorbable implants. The advantage of using resorbable polymers is that the polymers and thus the implant resorbs in the body and non-toxic degradation products will be metabolized by the metabolic system. One disadvantage of using non-reinforced resorbable polymers in implantable devices is the lack of mechanical strength and modulus, especially when compared with cortical bone. Another disadvantage of resorbable polymers is that they are not bioactive on their own. In order to achieve a bioactive bioresorbable polymer device, a bioactive compound or compounds, such as bioactive glass, needs to be added to the device. However, the addition of bioactive glass or other bioactive agents typically reduces the mechanical strength even to a lower level than that of the native polymer.

Self-reinforcing has been used to improve the strength of resorbable polymers and medical devices. Self-reinforcing is a polymer processing technique were the polymer molecules are forced to a certain orientation resulting in improved strength of the product. It has been reported that self-reinforced bioresorbable polymeric composites improve the strength of resorbable devices. Indeed, the composites showed relatively good mechanical properties, such as a bending strength of 360+/−70 MPa and a bending modulus of 12+/−2 GPa (P. Törmälä et al., Clinical Materials, Vol. 10, 1992, pp. 29-34), although the reported modulus values were still below the modulus values of strong cortical bone, the bending modulus of human tibial bone having been measured to be 17.5 GPa (S. M. Snyder and E. Schneider, Journal of Orthopedic Research, Vol. 9, 1991, pp. 422-431). The strength and strength retention of self-reinforced poly-L-lactic acid (SR-PLLA) composite rods were evaluated after intramedullary and subcutaneous implantation in rabbits. The initial bending strength of the SR-PLLA rods was 250-271 MPa. After intramedullary and subcutaneous implantation of 12 weeks the bending strength of the SR-PLLA implants was 100 MPa. (A. Majola et al., Journal of Materials Science: Materials in Medicine, Vol. 3, 1992, pp. 43-47).

In order to improve the mechanical strength of resorbable polymer based devices different types of fiber reinforced resorbable polymer composites have been developed. Poly (glycolic acid) (PGA), poly(lactide-co-glycolide) (PLGA), poly(lactic acid) (PLA) fibers in PLA or PDLA (poly(D-lactic acid)) matrix have been manufactured. The initial strength has been very good, however, the PGA and the PLGA fibers resorbed fast and the high strength was lost. Composites in which reinforcing fiber and the matrix were made of the same chemical composition have shown retention of the strength for longer periods of time. Polymer matrix degradation has been slowed down by increasing the hydrophobicity of the polymer and/or by addition of large quantities of buffering agents. Both techniques interfere with the interaction between phases and may result in weakening of the composite. (Publication WO 2008/067531)

However, Törmälä et al. in publication WO 2006/114483 have developed a composite material containing two reinforcing fibers, one polymeric and one ceramic, in a polymer matrix and reported good initial mechanical results, i.e. a bending strength of 420+/−39 MPa and a bending modulus of 21.5 GPa, which are the same level as for cortical bone. However, they have not reported any in vivo or in vitro hydrolytic behaviour and the prior art teaches that bioabsorbable composites, reinforced with absorbable glass fibers, have a high initial bending modulus but that they rapidly lose their strength and modulus in vitro.

The interaction of the hard brittle mineral phase and the flexible organic matrix gives bone its unique mechanical properties. The development of bone repairing materials or substitutes is typically oriented to combinations of mineral materials i.e. bioresorbable glasses to an organic polymeric matrix in order to generate a composite material exhibiting the toughness and flexibility of the polymer and the strength and hardness of the mineral filler and/or reinforcement. Numerous patents disclose the preparation and composition such a composite material (WO 2006/114483, U.S. Pat. No. 7,270,813, WO 2008/067531, WO 2008/035088).

The ultimate aim for a biomaterial in the field of bone and fracture fixation is that the material should mimic all the properties of bone, be bioactive, osteoconductive and biocompatible. Although the composite materials in prior art have led to the composite materials with attractive characteristics, they are still in need of improvement. At the moment, none of the prior art composites have been shown to possess in vivo mechanical properties comparable to natural bone.

A typical problem of the prior art composites is a poor polymer to reinforcement interface interaction and adhesion. The poor adhesion between the polymeric matrix and the ceramic reinforcement results in early failure at the interface in a physiological environment, and therefore the mechanical properties of the composite degrade too fast. Such degradation usually happens through hydrolysis of the interface. Therefore, improvement of the interfacial bonding (covalent bonding) is a key to the successful application of the biodegradable polymer composites to medical fields.

In the absence of a good interfacial adhesion between the polymer and inorganic reinforcement, transfer of stresses experienced by the load-bearing composite material from the elastic polymer to the stiff reinforcement will not appear. A lack of real covalent bonding/adhesion between the two phases results in early failure of mechanical properties in hydrolytic environment. Coupling agents, such as silanes, find their largest application in the composite industry, the compatibility between the reinforcement and polymer having long been known to be improved by using several types of surface coatings and coupling agents. Typically, any silane that enhances the adhesion of a polymer is often termed a coupling agent, regardless of whether or not a covalent bond is formed.

In the field of biomaterials, similar methods have recently been applied to improve the interface of hydroxyapatite or Bioglass®/polymer composites using coupling agents. However, in most of the cases, these treatments result in significant improvements in the ultimate stiffness of the composite (such as in WO 98/46164), but one major drawback lies in the fact that when the polymer matrix is made of biodegradable polymers they lack real covalent bonding between the reinforcement or filler and the polymer backbone and/or the reactive end-groups due to none-existence of them or low amount of them because of too high molecular weight (molecular weight of over 30 000 g/mol). Attempt to form covalent bonds into a weak polymer backbone typically leads to random chain scission, very low molecular weight fragments, gas evolution, unsaturation and autocatalytic degradation, which will ultimately lead to poor mechanical properties and thermal instability of the composite.

Moreover, similar type of methods have been applied to non-bioresorbable composites (see for example document U.S. Pat. No. 6,399,693). However, these materials are known to be highly resistant to hydrolysis and resorption both in vivo and in vitro. These materials would thus have similar disadvantages as metals and biostable materials, such as bone resorption and stress shielding when used as implant material in medical devices.

DEFINITIONS

The terms used in this application, if not otherwise defined, are those agreed on at the consensus conference on biomaterials in 1987 and 1992, see Williams, D F (ed.): Definitions in biomaterials: Proceedings of a consensus conference of the European Society for Biomaterials, Chester, England. Mar. 3-5, 1986. Elsevier, Amsterdam 1987, and Williams D F, Black J, Doherty P J. Second consensus conference on definitions in biomaterials. In: Doherty P J, Williams R L, Williams D F, Lee A J (eds). Biomaterial-Tissue Interfaces. Amsterdam: Elsevier, 1992. In this application, by bioactive material is meant a material that has been designed to elicit or modulate biological activity. Bioactive material is often surface-active material that is able to chemically bond with the mammalian tissues. A biodegradable material is a material that breaks down in vivo, but with no proof of its elimination from body.

The term bioresorbable in this context means that the material is disintegrated, i.e. decomposed, upon prolonged implantation when inserted into mammalian body and when it comes into contact with a physiological environment. The by-products of a bioresorbable material are eliminated through natural pathways either because of simple filtration or after their metabolisation. The terms bioresorbable and resorbable can be used interchangeably, but is it is clear that bioresorption is meant in this description. Especially, the term resorbable glass means silica-rich glass that does not form a hydroxyl-carbonate apatite layer on its surface when in contact with a physiological environment. Resorbable glass disappears from the body through resorption and does not significantly activate cells or cell growth during its decomposition process. By the term bioabsorbable it is meant a material that can dissolve in body fluids without any molecular degradation, and then excreted from the body.

By biomaterial is meant a material intended to interface with biological systems to evaluate, treat, augment or replace any tissue, organ or function of the body. By biocompatibility is meant the ability of a material used in a medical device to perform safely and adequately by causing an appropriate host response in a specific location, causing no foreign-body reactions and being non-toxic. By resorption is meant decomposition of biomaterial because of simple dissolution. By composite is meant a material comprising at least two different constituents, for example a polymer and a ceramic material, such as glass.

By melt derived glass fiber is meant the manufacturing of glass fibers where glass is molten in a crucible at 700-1700° C. and glass fibers are formed by pulling the molten glass through nozzles in the bottom of the crucible, which results in fibers with a diameter in the range of 5-300 micrometers.

In the present context the term medical devices relates to any kind of implant used within the body, as well as devices used for supporting tissue or bone healing or regeneration. An implant according to the present context comprises any kind of implant used for surgical musculoskeletal applications such as screws, plates, pins, tacks or nails for the fixation of bone fractures and/or osteotomies to immobilize the bone fragments for healing; suture anchors, tacks, screws, bolts, nails, clamps, stents and other devices for soft tissue-to-bone, soft tissue-into-bone and soft tissue-to-soft tissue fixation; as well as devices used for supporting tissue or bone healing or regeneration; or cervical wedges and lumbar cages and plates and screws for vertebral fusion and other operations in spinal surgery.

OBJECTS AND SUMMARY OF THE INVENTION

An object of the invention is to provide a composite wherein the above mentioned drawbacks have been minimized or even completely eliminated.

A further object of the invention is to provide a composite material usable in the manufacture of medical implants, which have a modulus at least as high as the modulus of the cortical bone so that the implant, once in use, is practically isoelastic with the bone.

An additional object of the present invention is to provide a composite material that does not have any or only negligible neuro and/or cytotoxic effects. A yet further object is to provide a material that has an increased biocompatibility compared to the materials known in the prior art.

A typical composite material according to the present invention comprises biocompatible and bioresorbable glass, a biocompatible and bioresorbable matrix polymer and a coupling agent capable of forming covalent bonds. It further comprises a compatibilizer, wherein at least 10% of the structural units of the compatibilizer are identical to the structural units of the matrix polymer, and the molecular weight of the compatibilizer is less than 30000 g/mol.

The invention also relates to the use of a composite material according to the present invention in the manufacture of a medical device, and to a medical device comprising a composite material according to this invention.

The invention further relates to a process for manufacturing a composite material according to this invention, comprising the steps of treating the surface of the glass by extraction with de-ionized water in order to remove ions from said surface, adding a coupling agent to the glass and reacting the glass with the coupling agent, adding a compatibilizer to the mixture of glass and coupling agent and reacting the coupling agent with the compatibilizer, and adding the polymer matrix material to the resulting mixture.

DETAILED DESCRIPTION OF THE INVENTION

A typical composite material according to the present invention comprises biocompatible and bioresorbable glass, a biocompatible and bioresorbable matrix polymer and a coupling agent capable of forming covalent bonds. It further comprises a compatibilizer, wherein at least 10% of the structural units of the compatibilizer are identical to the structural units of the matrix polymer, and the molecular weight of the compatibilizer is less than 30000 g/mol.

The invention thus provides composite materials that are useful as structural fixation for load-bearing purposes, exhibiting improved mechanical properties as a result of enhanced interfacial bonding and stability, unlike the composites described in prior art. Indeed, the disadvantages of the prior art are overcome or at least minimized by the present invention, which provides composite materials wherein a polymer matrix is bonded, with covalent bonds and physical entanglement, to biocompatible glass through a coupling agent and a low molecular weight compatibilizer.

The present invention provides a composite material in which the drawbacks of the prior art materials can be minimized or even eliminated, i.e. the composite retains its strength and modulus in vitro for a time period sufficient for bone healing for example. Indeed, with the present invention, high initial strength and modulus and good strength retention in vitro conditions can be achieved through true bonding between interfaces. Mechanical strength as used here includes bending strength, torsion strength, impact strength, compressive strength and tensile strength.

The invention also provides preparation methods that allow control over chemical and physical strength and stability of the bonds formed between the fiber glass and polymer matrix. The strength and stability of these bonds can be modified either by changing the coupling agent or by using a combination of coupling agents and/or the functionality of the compatibilizer. One way to modify the surface of the glass is to use a hydrophobic surface modifier together with a coupling agent and to use a re-crystallizable compatibilizer which will form crystals and/or spherulites inside the polymer matrix phase (spherulites are spherical semi-crystalline regions inside a polymer matrix).

If the hydrolytic stability of the oxane bond between the silane and the glass needs to be enhanced or the device is in an aggressive aqueous environment, dipodal silanes often exhibit substantial performance improvements. These materials form tighter networks and may offer up to 100 000 times greater hydrolysis resistance than conventional coupling agents (with the ability to form only three bonds to a substrate). Inorganic fillers or reinforcements, such as calcium carbonate and high phosphate and sodium glasses, are usually not suitable for silane coupling agents. Moreover, high phosphate and sodium containing glasses are frequently the most frustrating glass substrates in terms of coupling agent and surface modification reactions. The primary inorganic constituent of glass is silica and it would be expected to react readily with silane coupling agents. However, alkali metals and phosphates do not only form hydrolytically stable bonds with silicon, but, even worse, catalyze the rupture and redistribution of silicon-oxygen bonds. The first step in coupling with these substrates is thus the removal of ions from the surface by extraction with de-ionized water. Hydrophobic dipodal or multipodal silanes are usually used in combination with organofunctional silanes. In some cases polymeric silanes with multiple sites for interaction with the substrate are used (Gelest Inc. Silane Coupling Agents: Connecting Across Boundaries).

According to another embodiment of the present invention the composite material may comprise two or more types of resorbable and biocompatible glasses, each type having a different composition. The composite may also comprise at least one biocompatible and bioresorbable glass and at least one bioactive, biocompatible and bioresorbable glass, the glasses having different compositions.

A second type of glass can be for example a glass having higher bioactivity and resorption rate, which can be in the form of granules, spheres, blocks or fibers. In the case of a faster resorption rate and a higher bioactivity, the main function is not the reinforcement of the composite, but instead to be a more osteoconductive material, which means that it promotes and facilitates bone healing, in the form of granules and/or powder, such as for example BonAlive®.

The composite material may also comprise two or more types of polymers, two or more types of coupling agents and two or more types of compatibilizers. Moreover, the composite material may also comprise the glass in the form of two or more groups of fibers having different median diameters.

Compatibilizer

The term compatibilizer as is used in this description refers to a low molecular weight polymer, which has structural units at least partly identical to those in the polymer matrix. The structural units can also be completely identical to the one in the polymer matrix material, but the molecular weight is lower. Indeed, the molecular weight of the compatibilizer is at most 60% of the molecular weight of the matrix polymer material and less than 30 000 g/mol. The molecular weight used here is the average molecular weight. A preferable molecular weight of the compatibilizer is less than 10000 g/mol.

According to the invention, at least 10% of the structural units of the compatibilizer are identical to the structural units of the matrix polymer. According to another embodiment of the invention, at least 20, 30, 50 or 60% of the structural units of the compatibilizer are identical to the structural units of the matrix polymer.

The compatibilizer is typically a functionalized molecule that can be a linear, branched, grafted, star shaped, hyperbranched or dendritic polymer. For example, low molecular weight PLLA can act as a compatibilizer for a PLGA, PLLA/PCL or PLLA polymer matrix and it forms physical entanglements and/or crystals inside the polymer matrix.

A typical compatibilizer is a low molecular weight resorbable polyester. Molecular weights are typically less than 30 000 g/mol, preferably less than 20 000 g/mol, more preferably less than 10 000 g/mol and most preferably 2000-8000 g/mol. The end-group functionality is preferably hydroxyl, vinyl or carboxylic acid. Low molecular weight is necessary in order to have a high amount of end-groups available for the reaction with the coupling agent, and on the other hand reasonable length is required for the creation of physical interactions i.e. to form chain entanglements or enable the crystallization within the polymer matrix. The structure of the compatibilizer can also vary according to the alcohol used as a co-initiator in polymerization. Mono- and difunctional alcohols typically yield linear polymers, whereas alcohols with hydroxyl functionality higher than two usually give comb-shaped, star-shaped, hyper branched or dendritic polymers. Also other functionalized compatibilizers can be used.

The following examples of functionalization of the compatibilizer are illustrative but not limiting the compositions and/or methods of the invention. A hydroxyl terminated compatibilizer can be reacted with methacrylic anhydride or butanediisocyanate to form methacrylic and isocyanate functionality respectively to the compatibilizer. Such methods and chemistry thereof are described in A. Helminen, Branched and crosslinked resorbable polymers based on lactic acid, lactide and ε-caprolactone; Polymer Technology Publication series No. 26, Otamedia 2003 and Seppälä et al. publication WO 2006/53936. These functionalized end-groups in a compatibilizer will then react with the coupling agents with or without catalyst, such as free radical initiators or acids or bases.

According to an embodiment of the invention, the amount of the compatibilizer is 0.1-20 weight-%, preferably 0.25-10 weight-%, and most preferably 0.5-2 weight-% of the total weight of the composite material.

As described above it is necessary to use a compatibilizer that enables covalent bonding between the polymeric phase and the glass phase. An additional advantage of the compatibilizer is to further protect the glass and also act as a lubricant in the manufacturing process. When chopped fibers are used, the compatibilizer can prevent the imminent risk of agglomeration of the short length fibers.

In the case of using continuous fibers as reinforcement, the compatibilizer may be added online in the fiber drawing process, but when cut/chopped fibers are manufactured a slurry process is preferred as is used in standard manufacturing processes of biostable chopped E-, S-, C-glass fibers.

Biocompatible and Bioresorbable Glass

Different biocompatible and resorbable glasses can be used in this invention. Bioresorbable and biocompatible glass can also be bioactive. The glass can be for example in the form of fibers, dust, powder, granules and spheres, typical being the fiber form.

The selection of biocompatible and resorbable glass is typically based on two facts, firstly that the resorption rate is slow combined with a slow pH increase in a physiological environment which will not cause degradation of the polymer matrix and rupture of covalent bonds in the surface of the fiber glass. Secondly, the mechanical strength and the amount of reactive hydroxyl groups of the glass need to be sufficient. The amount of hydroxyl groups on the surface of the fiber glass can be ensured for example by online de-ionized water-spray treatment during the fiber manufacturing process (schematic presentation of the fiber drawing process is described in FIG. 1 and in detail in document EP 1 958 925).

In general, the resorption of degradable glasses is a function of the composition and of the surface to volume ratio i.e.

surface erosion by a physiological environment. Due to high surface to volume ratio of fibers and powders, it is necessary to know and to be able to control the resorption rate of the glass and release of alkali and alkali earth metal ions to the physiological environment. Alkali metal ions are responsible for high local pH increase and in certain cases may cause physiological problems as neurotoxic and cytotoxic effects, especially when potassium is present in the glass.

The omission of potassium from a melt derived glass fiber and powder composition will increase its biocompatibility and eliminate neurotoxic and cytotoxic effects. Furthermore, by varying the amount of silica and other components i.e. $Na_2O$, $CaO$, $MgO$, $P_2O_5$, $B_2O_3$, $Al_2O_3$ and $Li_2O$ in the glass composition, the resorption rate of the glass fibers can be easily controlled and tailor-made for diverging end applications.

A typical potassium free resorbable melt derived glass composition suitable for the present invention comprises

| | |
|---|---|
| $SiO_2$ | 60-70 weight-%, |
| $Na_2O$ | 5-20 weight-%, |
| $CaO$ | 5-25 weight-%, |
| $MgO$ | 0-10 weight-%, |
| $P_2O_5$ | 0.5-5 weight-%, |
| $B_2O_3$ | 0-15 weight-%, |
| $Al_2O_3$ | 0-5 weight-% and |
| $Li_2O$ | 0-1 weight-% |

Resorbable and biocompatible melt derived glass fibers suitable for the present invention can be manufactured from such resorbable glass compositions. Document EP 1 958 925, the contents of which are hereby incorporated, describes one of the technologies enabling the manufacture of a wide range of resorbable and bioactive glasses while circumventing the problems relating to crystallization during fiber production. These fibers show improved strength properties, when compared for example to polymer fibers having the same diameter. According to one embodiment of the invention, suitable glass fibers show a tensile strength of 800-2000 MPa.

According to one aspect of the invention, important features of the resorbable and biocompatible fiber glass used in the present composite are the amounts of $SiO_2$ and $Na_2O$, $SiO_2$ amount should be kept at quantities preferably between 60 and 70 weight-% to sustain a required amount of reactive hydroxyl groups in the surface of the fiber glass in order to enable a reaction between the coupling agent and the fiber glass.

Moreover, on one hand $Na_2O$ and $P_2O_5$ amounts should be relatively low due to the fact that alkali metals and phosphates do not only form hydrolytically stable bonds with silicon, but, even worse, catalyze the rupture and redistribution of silicon-oxygen bonds. On the other hand, sodium is necessary for sustaining the resorbability of the glass fiber without giving rise to high amounts of released alkali metals, thus preventing a detrimental or toxicological local pH peak in physiological environment. In addition, phosphorous calcium oxides are needed in sufficient amounts to retain long term bioactivity i.e. formation of CaP.

There are thus two types of biocompatible resorbable glasses; one type "only" resorbs and the other type resorbs and is bioactive (osteoconductive). It is believed that a prerequisite for a glass to bond to bone is the formation of a calcium phosphate rich layer at the glass surface which is in contact with the body fluid. The initially formed amorphous calcium phosphate crystallizes with time to hydroxyl apatite, hydroxy apatite being the main constituent of a bone. The selection of one or more glass types depends on the application for the composite. In a bone screw type of medical device both bioactivity and resorbability are wanted properties: the screw will be slowly replaced by own bone and no empty cavity should remain. In a wrist plate type of medical device, the bioactivity is an unwanted characteristic because bone growth over and inside the plate would be harming the function of the arm.

Biocompatible and resorbable glass is typically used in the form of fibers. The diameter of the fibers suitable for the present invention is less than 300 µm, typically 1-75 µm, more typically 5-30 µm, preferably 10-25 µm, more preferably 10-20 µm. The fibers can be used as long single fibers, as yarns, braids, rovings, and bands or as different types of fabrics made by using the methods of textile technology (mats, felts, nonwoven, woven etc.). The fibers can also be used as chopped fibers and mats or textiles manufactured from chopped fiber.

According to one embodiment of the invention the length of chopped fibers is less than 20 mm, typically 0.5-10 mm, more typically 1-5 mm, preferably 2-3 mm, and usually approximately 2.5 mm. According to another embodiment of the invention the length of continuous fibers is over 20 mm, preferably over 30 mm, usually more than 40 mm or most preferably as fully continuous fiber in pultrusion, for example.

According to an embodiment of the invention, the amount of resorbable and to biocompatible glass is 1-90 weight-%, preferably 10-80 weight-%, more preferably 20-70 weight-% and most preferably 30-60 weight-% of the total weight of the composite material.

When a mixture of resorbable and bioactive glass fibers is used, the amount of reinforcing glass fibers is usually over 10 volume-%, preferably over 40 volume-%, more preferably over 60 volume-%, most preferably over 90 volume-% of the total volume of the fibers of the composite material. Their orientation can also be freely chosen depending on the intended use.

Coupling Agent

The term coupling agent as used in the text refers to compounds capable of forming covalent bonds. Typically, the coupling agent is a silane, and usually the covalent bond is formed between the glass and the coupling agent, and between the coupling agent and the compatibilizer.

The general formula of an organosilane shows two classes of functionality.

$$RnSiX(4-n)$$

The X functional group is involved in the reaction with the inorganic substrate. The bond between X and the silicon atom in the coupling agent is replaced by a bond between the inorganic substrate and the silicon atom. X is a hydrolysable group, typically alkoxy, acyloxy, amine or chlorine. The most common alkoxy groups are methoxy and ethoxy, which give methanol and ethanol as by-products during coupling reactions.

R is a non-hydrolysable organic radical that possesses a functionality which enables the coupling agent to bond with polymers. Most of the widely used organosilanes have one organic substituent. On the other hand, inorganic surfaces can impose important steric constraints on the accessibility of organic functional groups in close proximity. If the linker length is important, the functional group has greater mobility and can extend further from the inorganic substrate. This has important consequences, if the functional group is expected to react with a single component in multi-component organic or aqueous phases (UCT Specialties, LLC., Silane coupling agent guide).

Functional dipodal silanes and combinations of non-functional dipodal silanes with functional silanes have significant impact on substrate bonding, hydrolytic stability and mechanical strength of many composites systems. The general formula of dipodal silanes shows also two classes of functionality except that dipodal silanes have more hydrolysable groups, usually six, than conventional silane coupling agents (Gelest Inc. Silane Coupling Agents: Connecting Across Boundaries).

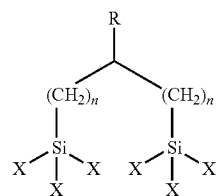

In most cases the silane is subjected to hydrolysis prior to the surface treatment. Following hydrolysis, a reactive silanol group is formed, which can condense with other silanol groups, for example, those on the surface of siliceous reinforcements and/or fillers, to form siloxane linkages.

Water for hydrolysis may come from several sources. It may be added, it may be present on the substrate surface or it may come from the atmosphere. Hydroxyl-containing substrates vary widely in concentration and type of hydroxyl groups present. Freshly fused substrates stored under neutral conditions have a minimum number of hydroxyls. Hydrogen bonded vicinal silanols react more readily with silane coupling agents, while isolated or free hydroxyls react reluctantly.

Organofunctional silanes used as coupling agents or primers for the adhesion of to organic polymers to mineral substrates are almost invariably used at more than mono-layer coverage of the mineral surface. Regardless of the method of application, they condense on the mineral surface to build an oligomeric siloxane network capable of forming covalent "oxane" bonds to the mineral surface. The oligomeric siloxane (condensed silane) layer is modified by its reactions with the compatibilizer during the surface treatment.

The resulting interfacial region preferably has certain characteristics for optimum performance. For example, oxane bond formation with the mineral surface should be completed. This may require controlled drying at an elevated temperature or use of a catalyst. Moreover, the interphase region should preferably have low water absorption, best accomplished by incorporating hydrophobic substituents in the coupling agents.

In the present invention, it is possible to use also surface modifiers capable of protecting the glass and to increase the wetting of the glass. In this case, alkyl- and arylsilanes are used as surface modifiers, as they are not considered coupling agents in the present sense, because they do not contain functional groups which would react with the compatibilizer. Surface modification (i.e. modification of hydrophobicity, hydrophilicity or oleophilicity) with these non-functional materials can have profound effects on the interphase. They are used to alter surface energy or wetting characteristics of the substrate. In the reinforcement of polymers with glass fibers, one approach for optimizing reinforcement is to match the critical surface tension of the silylated glass surface to the surface tension of the polymer in its melt or uncured condition. This has been most helpful in polymers with no obvious functionality (E. P. Plueddemann, Silane coupling agents $2^{nd}$ ed., Kluwer 1991). A surface modifier thus protects the glass from degradation and mechanical stresses. It is especially useful in case of highly degradable glasses, and while improving the wetting, it also improves the adhesion, via physical interactions.

Some important aspects for the selection and the use of combination of two or more coupling agents and optionally of surface modifiers are to ensure covalent bonding with the compatibilizer and to protect the glass against the early rupture caused by water or body fluids, thus still maintaining the required degradation and long-term bioactivity. Another aspect of using coupling agents and/or silane surface modifiers is to achieve optimal wetting properties of the glass surface, protect the glass from stresses and aid further processing with the compatibilizer and ultimately the polymer matrix. If particular hydrolytic stability is required by the end application, dipodal silanes can be used in the mixture of coupling agent and silane surface modifiers. Due to biocompatibility, ethoxy groups are preferred instead of methoxy groups as the hydrolysable group in silanes, although they are less reactive than methoxy groups. In the case of continuous fibers as a reinforcement, the coupling agents and silane surface modifiers can be added online in the fiber drawing process, but when cut/chopped fibers are manufactured, a slurry process is preferred.

Below is a short list of functionalities of silane coupling agents and silane surface modifiers as examples which can be used in the present invention.

Alkanoamines such as bis(2-hydroxyethyl)-3-aminopropyltriethoxysilane

Alkyls (surface modifier), such as 3-propyltriethoxysilane, octyltriethoxy-silane, isobutyltriethoxysilane, isooctyltrimethoxysilane Allyls, such as allyltrimethoxysilane Amines, such as N-(2-aminoethyl)-3-aminopropylmethyldimethoxysilane, N-(2-aminoethyl)-3-aminopropyltrimethoxysilane, 3-am inopropylmethyl-diethoxysilane, 3-aminopropyltriethoxysilane, 3-aminopropyltrimethoxysilane, (N-trimethoxysilylpropyl)polyethyleneimine, trimethoxysilylpropyldiethylenetriamine, n-butylamino-propyltrimethoxysilane Anhydrides, such as 3-(triethoxysilyl)propylsuccinic anhydride Aromatics (surface modifier), such as phenyltriethoxysilane, phenyltri-methoxysilane Chloroalkyls, such as 3-chloropropyltrimethoxysilane Chloromethylaromatics, such as 1-trimethoxysilyl-2(p,m-chloromethyl)-phenyl-ethane Dipodals, such as bis(trimethoxysilylpropyl)amine, bis(triethoxysilyl-ethyl)vinylmethylsilane, bis(triethoxysilyl)ethane, 1-(triethoxysilyl)-2-(diethoxymethylsilyl)ethane Epoxy, such as 2-(3,4-epoxycyclohexyl)ethyltrimethoxysilane, 3-glycidoxypropyltrimethoxysilane, 3-glycidoxypropyltriethoxysilane Fluoroalkyls (surface modifier), such as 3,3,3-trifluoropropyltrimethoxy-silane Isocyanates, such as isocyanotopropyltriethoxysilane Mercapto, such as bis[3-(triethoxysilyl)propyl]tetrasulfide, 3-mercaptopropylmethyldimethoxysilane, 3-mercaptopropyltrimethoxysilane Methacrylates, such as 3-methacryloxypropyltriethoxysilane, (3-acryloxy-propyl)trimethoxysilane Phosphine, such as 2-(diphenylphosphino)ethyltriethoxysilane Silazanes (surface modifier), such as 1,3-divinyltetramethyldisilazane, hexamethyldisilazane Styryls, such as 3-(N-styrylmethyl-2-aminoethylamino) propyltrimethoxy-silane hydrochloride Ureidos, such as N-(triethoxysilylpropyl)urea Vinyls, such as vinyltriethoxysilane, vinyltrimethoxysilane, vinyltris(2-methoxyethoxy)silane According to an embodiment of the invention, the amount of coupling agent is 0.1-10 weight-%, preferably 0.1-8 weight-% and most preferably 0.2-5 weight-% of the amount of glass fiber.

The difference between a coupling agent and a modifier in the present application is present in their molecular formula: a coupling agent contains one to three hydrolyzable groups and at least one organoreactive group (able to form covalent bonds) which can react with a reactive site of the polymer i.e. the R group is a nonhydrolyzable organic radical that possesses a functionality that imparts the desired characteristics. This includes the ability to effect a covalent bond between the organic polymer and inorganic materials. On the other hand, a modifier contains also one to three hydrolyzable groups, but also at least one non-functional hydrocarbon group (i.e. alkyl and/or aryl groups). Alkyl- and arylsilanes are not considered coupling agents in the present description. Surface modifications with these non-functional materials have significant effects on the interphase. They are used to alter the surface energy or wetting characteristics of the substrate. The property modifications include: hydrophobicity, release, dielectric, absorption, orientation, hydrophilicity and charge conduction.

As an example, the following definition can be given.

A coupling agent has a general formula of $R1-(CH_2)_n-Si-X_3$, a modifier has a general formula of $R2-(CH_2)_n-Si-X_3$, wherein R1=an organofunctional group
R2=a non-functional hydrocarbon
$(CH_2)_n$=a linker
Si=a silicon atom
X=a hydrolyzable group As known in the field of glass fiber reinforced composites, hydrolytic instability of the oxane bond between the silane and the glass plays a major role in the degradation mechanism of glass and is affected by water, basic and acidic ions from the surrounding environment and from the glass itself. By losing the adhesion (bonding) between the glass and the polymer matrix the composite will lose its mechanical strength and in order to have suitable biomaterial it has to be controllable to suit for the proper medical device application. The selection of suitable hydrophobic non-functional silanes will prevent hydrolysis of surface molecules by keeping the water away from the glass surface. The compatibilizer is less hydrophobic than the surface modifier. However, the compatibilizer will be more compatible with polymer and will create the physical link between the matrix and the inorganic material.

Bioresorbable and Biocompatible Polymer

The composite material according, to the present invention comprises a polymer matrix, preferably a continuous polymer matrix, but not excluding discontinuous polymer matrix, in which the polymer matrix is biocompatible and resorbable. The biocompatible glass material, which is typically in the form of fibers, is embedded in the polymer matrix, which means that the surfaces of the fibers are covered by said polymer. Preferably, at least 80% of the surfaces of the fibers are covered by the polymer matrix, more preferably at least 90%, and most preferably at least 95% of the surfaces of the fibers are covered by the polymer matrix. Preferably also at least 99% of the surfaces of the fibers of the composite material are covered by the polymer matrix.

The molecular weight of the polymer is over 30000 g/mol, and preferably over 40000 g/mol.

Polylactide (i.e. poly(lactic acid), PLA), polyglycolide (PGA) and poly(ε-caprolactone) (PCL), and their co- and terpolymers are among the most common, well studied and used resorbable polymers. These high molecular weight polyesters are typically produced by the ring-opening polymerization of the cyclic monomers, i.e. lactide, ε-caprolactone and glycolide.

Poly(L-lactide) homopolymer is a semicrystalline polymer having a melting temperature $T_m$ around 180° C. and a glass transition temperature $T_g$ of 60-65° C. Poly(DL-lactide) homopolymer is an amorphous polymer having $T_g$ 55-60° C. PLA has the characteristics of a glassy, stiff but brittle material having a tensile strength of 65 MPa and Young's modulus of 3-4 GPa.

PCL is a strong, ductile rubbery polymer with low melting temperature of 60° C. and $T_g$ −60° C., tensile strength of 40 MPa and modulus of 0.4 GPa.

PGA has the characteristics of a glassy, stiff but brittle material having a low melting point of 215-225° C. and $T_g$ 40° C., as well as a tensile strength of 100 MPa and Young's modulus of 3-4 GPa.

Co- and terpolyesters of PLA, PGA and PCL are of interest in the tailoring of the optimal polymer for resorbable composite material for medical devices. The choice of monomer ratio and molecular weight significantly affects the strength elasticity, modulus, thermal properties, degradation rate and melt viscosity.

All of these polymers are known to be degradable in aqueous conditions, both in vitro and in vivo. Two stages have been identified in the degradation process; First, degradation proceeds by random hydrolytic chain scission of the ester linkages which decreases the molecular weight of the polymers. In the second stage measurable weight loss in addition to chain scission is observed. The mechanical properties are mainly lost or at least a remarkable drop will be seen in them at the point where weight loss starts. Degradation rate of these polymers is different depending on the polymer structure: crystallinity, molecular weight, glass transition temperature, block length, racemization and chain architecture (J. C. Middleton and A. J. Tipton, Biomaterials 21, 2000, 2335-2346).

According to the present invention, the following resorbable polymers, copolymers and terpolymers may be used as a matrix material for the composite. For example, polylactides (PLA), poly-L-lactide (PLLA), poly-DL-lactide (PDLLA); polyglycolide (PGA); copolymers of glycolide, glycolide/trimethylene carbonate copolymers (PGA/TMC); other copolymers of PLA, such as lactide/tetramethylglycolide copolymers, lactide/trimethylene carbonate copolymers, lactide/d-valerolactone copolymers, lactide/ε-caprolactone copolymers, L-lactide/DL-lactide copolymers, glycolide/L-lactide copolymers (PGA/PLLA), polylactide-co-glycolide; terpolymers of PLA, such as lactide/glycolide/trimethylene carbonate terpolymers, lactide/glycolide/ε-caprolactone terpolymers, PLA/polyethylene oxide copolymers; polydepsipeptides; unsymmetrically 3,6-substituted poly-1,4-dioxane-2,5-diones; polyhydroxyalkanoates, such as polyhydroxybutyrates (PHB); PHB/b-hydroxyvalerate copolymers (PHB/PHV); poly-b-hydroxypropionate (PHPA); poly-p-dioxanone (PDS); poly-d-valerolactone-poly-ε-caprolactone, poly(ε-caprolactone-DL-lactide) copolymers; methylmethacrylate-N-vinyl pyrrolidone copolymers; polyesteramides; polyesters of oxalic acid; polydihydropyrans; polyalkyl-2-cyanoacrylates; polyurethanes (PU); polyvinylalcohol (PVA); polypeptides; poly-b-malic acid (PMLA); poly-b-alkanoic acids; polycarbonates; polyorthoesters; polyphosphates; poly(ester anhydrides); and mixtures thereof; and natural polymers, such as sugars, starch, cellulose and cellulose derivatives, polysaccharides, collagen, chitosan, fibrin, hyalyronic acid, polypeptides and proteins. Mixtures of any of the above-mentioned polymers and their various forms may also be used.

The polymer material can be porous or it can become porous during the use and/or when in contact with the tissue.

According to an embodiment of the invention, the amount of the matrix polymer is 1-90 weight-%, preferably 10-80 weight-%, more preferably 20-70 weight-% and most preferably 30-60 weight-% of the total weight of the composite material.

The present invention also relates to the use of a composite material according to this invention in the manufacture of a medical device. The invention also relates to a medical device comprising a composite material as explained above. The medical device can be for example an implant. The devices according to the invention, manufactured from the composite of this invention, having high initial modulus and good strength retention in vitro are useful in manufacturing of e.g. bone fracture fixation devices, because high initial modulus and strength retention under hydrolytic conditions provide the devices with initial isoelastic behavior in comparison to the healing bone.

The medical device can be any kind of implant used within the body or a device for supporting the tissue or bone healing and/or regeneration. The medical device can also be any kind of textile, woven or non-woven, to be used within the body.

An implant according to the present context comprises any kind of implant used for surgical musculoskeletal applications, such as screws, plates, pins, tacks or nails, for the fixation of bone fractures and/or osteotomies to immobilize the bone fragments for healing; suture anchors, tacks, screws, bolts, nails, clamps, stents and other devices for soft tissue-to-bone, soft tissue-into-bone and soft tissue-to-soft tissue fixation; as well as devices used for supporting tissue or bone healing or regeneration; or cervical wedges and lumbar cages and plates and screws for vertebral fusion and other operations in spinal surgery.

According to the present invention the composite material can also be used as a porous tissue engineering scaffold. Preferably, the scaffold has a porosity degree of 60%, more preferably at least 80%, and most preferably at least 90%.

The advantage of medical devices according to the present invention is that they disappear from the body by degradation without giving rise to toxic effects through a high local pH peak and the release of potassium.

Depending on the application and purpose of the medical device material, the medical devices, in addition to being biocompatible, also exhibit controlled resorption in the mammalian body. The optimal resorption rate is directly proportional to the renewal rate of the tissue in the desired implantation location. In the case of bone tissue, a considerable proportion of the implant is preferably resorbed/decomposed within 3 to 12 months in the tissue. In cases where physical support to the healing tissues is desirable, the resorption rate might be several months or even several years. Furthermore, the invention can be made use of in medical devices such as canules, catheters and stents. The invention can also be made use of in fiber-reinforced scaffolds for tissue engineering.

Another advantage of the medical devices according to the invention is their strength and feasible manufacturing. Medical device according to the present invention can be manufactured by arranging fibers in a resorbable polymer matrix and using any type of polymer processing equipment e.g. an open or closed batch mixer or kneader, continuous stirring tank reactor or mixer, extruder, injection molding machine, reactive injection molding (RIM), lamination, calenders, transfer molding, compression molding, mechanical machining, pultrusion, solvent casting, tube reactor or other standard melt processing or melt mixing equipment known in the field producing and/or shaping into an implant having a desired orientation of the continuous fibers and/or chopped/cut fibers and/or woven, non-woven mats/textiles.

One further advantage of the present invention is that the melting temperature of the matrix material is around 30-300° C., and the glass transition temperature of the fibers around 450-750° C. Consequently, the glass fibers are not damaged by the temperature of the melted matrix material and a strong fiber-reinforced medical device is obtained when the matrix is allowed to solidify.

In order to modify the degradation of the final implants, to enhance their surface properties, or to add biologically active compounds, such as bioactive glass, hydroxyl apatite and/or tricalciumphosphate therein, they can be further modified by an additional resorbable polymer coating layer with a process that may include co-extrusion, dipcoating, electrospraying, injection molding, critical solution impregnation or any other known technique used in polymer, pharmaceutical, device or textile industry. The polymers may be those mentioned above.

The present invention yet further relates to a process for manufacturing a composite material according to this invention, the process comprising the steps of
  treating the surface of the glass by extraction with de-ionized water in order to remove ions from said surface,
  adding a coupling agent to the glass and reacting the glass with the coupling agent,
  adding a compatibilizer to the mixture of glass and coupling agent and reacting the coupling agent with the compatibilizer,
  adding the polymer matrix material to the resulting mixture.

The process may also comprise, at the end, a step of removing solvents from the composite obtained as well as another additional step of surface treatment of the composite.

Treating the surface of the glass by extraction with de-ionized water in order to remove ions from said surface is a useful step, because in biodegradable glasses the primary inorganic constituent is silica and it would be expected to react readily with silane coupling agents. However, alkali metals and phosphates not only do not form hydrolytically stable bonds with silicon, but, even worse, catalyze the rupture and redistribution of silicon-oxygen bonds. On the other hand, de-ionized water treatment is needed to form hydroxyl groups on the surface of the glass due to the fact that freshly melt-derived biodegradable glass fibers, under neutral conditions, have a minimum number of hydroxyl groups which are however important for reactions between the coupling agent and the biodegradable glass fiber.

The process for manufacturing a composite material according to this invention can be used continuously or batchwise.

The embodiments and variants described above in connection with any of the aspects of the present invention apply mutatis mutandis to the other aspects of the invention.

In this specification, except where the context requires otherwise, the words "comprise", "comprises" and "comprising" means "include", "includes" and "including", respectively. That is, when the invention is described or defined as comprising specified features, various embodiments of the same invention may also include additional features.

Embodiments of the present invention will now be described in detail in the following examples of the Experimental part. The examples are illustrative but not limiting the compositions, methods, applications and use of the present invention.

EXPERIMENTAL PART

General manufacture of a biodegradable glass preform (300 g) was made according to the following procedure: dry-mix of raw materials, melting in a platinum crucible in a furnace, annealing, crushing, re-melting and annealing. The raw material sources used were $SiO_2$, $Al_2O_3$, $Na_2CO_3$, $(CaHPO_4)(H_2O)$, $CaCO_3$, $H_3BO_3$ and $MgO$.

The fiber drawing was conducted according to the method described in the patent application EP 1 958 925, except that a thin spray of de-ionized water was applied to the hot fibers as shown in FIG. 1. The manufacturing process is shown in more detail in FIG. 1, wherein the glass is fed to a crucible 1 from which it is drawn to fibers 2. The fibers 2 are treated with de-ionized water 3 and further with the coupling agent 4. The reaction between the coupling agent and the glass occurs in a furnace 5. After this, the compatibilizer 6 is added to the resulting fibers and the ensuing reaction takes place in a second furnace 7. The polymer material 8 is then added to the fibers which are again conducted to a third furnace 9. The resulting fibers are then collected by spooling at 10.

According to the general procedure described above, mixtures having components in the following composition range were used for manufacturing the preform, which was then used for manufacturing reinforcing fiber:

| | |
|---|---|
| $SiO_2$ | 60-70 weight-%, |
| $Na_2O$ | 5-20 weight-%, |
| $CaO$ | 5-25 weight-%, |
| $MgO$ | 0-10 weight-%, |
| $P_2O_5$ | 0.5-5 weight-%, |
| $B_2O_3$ | 0-15 weight-%, |
| $Al_2O_3$ | 0-5 weight-% |

Example 1

Composition and Manufacture of a Resorbable Glass Fiber

According to the general procedure described above, the following glass composition to was manufactured and drawn into fiber form.

| | |
|---|---|
| $SiO_2$ | 64.0 weight-%, |
| $Na_2O$ | 11.0 weight-%, |
| $CaO$ | 18.0 weight-%, |
| $B_2O_3$ | 2.0 weight-% |
| $MgO$ | 2.0 weight-% |
| $P_2O_5$ | 0.5 weight-%, |
| $Al_2O_3$ | 2.5 weight-%, |

After drawing, the fibers were stored in foil bags under protective gas and stored for further analyses and use. The composition and amorphous nature was confirmed using X-ray fluorescence (XRF) and X-ray diffraction (XRD), respectively. The average fiber diameter was about 35 µm.

Example 2

Manufacturing on-Line Surface-Treated Resorbable Glass Fiber

Resorbable glass fibers were manufactured according to Example 1 except that the fibers were surface treated on-line with a solution of a coupling agent in ethanol and water, namely 5 wt-% of the coupling agent 3-glycidoxypropyltriethoxysilane, 90 wt-% of ethanol and 5 wt-% of water, the solution being catalyzed with acetic acid (pH 4.5). The fiber was then cured on-line and dried to complete the reaction. The surface treatment was confirmed by contact angle measurement.

Example 3

Manufacturing on-Line Surface Treated Resorbable Glass Fiber

Resorbable glass fibers were manufactured according to Example 1, except that fibers were surface treated on-line with a solution of a coupling agent, surface modifier, ethanol and water, namely 5 wt-% of a mixture of the coupling agent 3-glycidoxypropyltriethoxysilane and the surface modifier n-propyltriethoxysilane (in a ratio or 2:1), 90 wt-% of ethanol and 5 wt-% of water, catalyzed with acetic acid (pH 4.5). The fibers were then cured on-line at a temperature of 200° C. and dried at a temperature of 150° C. to complete the reaction. The surface treatment was confirmed by contact angle measurement.

Example 4

Manufacturing Surface and on-Line Compatibilizer Treated Resorbable Glass Fiber

Resorbable glass fibers were manufactured according to Example 3, except that after the surface treatment, a compatibilizer was added on-line. The compatibilizer used was poly (L-lactide), with a molecular weight of 2000 g/mol and was used as a 1 wt-% solution in ethyl acetate, catalyzed with 0.02 mol-% tin(II)-ethylhexanoate. The fibers were then cured on-line and dried at a temperature of 120° C. The compatibilizer treatment was confirmed by contact angle measurement and Fourier transformation infrared (FTIR).

Example 5

Manufacturing Polymer Coated Resorbable Glass Fiber

Resorbable glass fibers were manufactured according to Example 4, except that after adding the compatibilizer polymer, PLGA inherent viscosity (i.v.) 2,3 coating was added on-line as 8 wt-% solution in ethyl acetate. The polymer coating was detected with a microscopic method and the fibers were observed to form a firm polymer-coated bundle.

Example 6

Manufacturing a Resorbable Continuously Reinforced Composite Rod

A composite rod (having a diameter of 2 mm) was manufactured with twin screw extruder equipped with a crosshead die to feed the polymer coated glass fiber bundles into the molten matrix polymer. The matrix polymer and the polymer coating were made from the same polymer that was grade PLGA i.v. 2,3. The extruder barrel temperatures were 185° C./175° C./175° C. and the die temperature was 190° C. The fiber content was 38 wt-%.

Example 7

Manufacturing Surface and Compatibilizer Treated Resorbable Glass Fiber with a Slurry Process Resorbable glass fibers were manufactured according to Example 1 and chopped to 10 mm length. Chopped fibers were fed into a 2 L rotary evaporator vessel and surface treated with a 5 wt-% mixture of a coupling agent vinyltriethoxysilane and a surface modifier n-propyltriethoxysilane (in a ratio of 2:1), as a solution in 90 wt-% ethanol and 5 wt-% water, catalyzed with acetic acid (pH 4.5). After the reaction was is complete, a solvent change was conducted, changing the solvent to ethyl acetate and a compatibilizer was added together with a radical initiator (benzoyl peroxide, 0.1 wt-%). The compatibilizer was 1 wt-% methacrylate functionalized PLLA having a molecular weight of 2000 g/mol. After the reaction was complete, the surface and compatibilizer treated glass fiber was filtered and dried. The compatibilizer treatment was confirmed by contact angle measurement and FTIR Example 8

Manufacturing a Resorbable Chopped Fiber Reinforced Composite Rod

A composite rod (having a diameter of 4 mm) was manufactured with a twin screw extruder equipped with a side feeder for the treated chopped fiber. 70/30 L-lactide/ε-caprolactone copolymer as polymer matrix was used with a 50:50 ratio to chopped fiber. The barrel temperatures were 175° C./165° C./160° C. and the die temperature was 160° C.

Example 9

Manufacturing a Resorbable High Bioactive Textile Reinforced Composite Plate

Two types of resorbable glass fibers were manufactured, one glass composition with a higher bioactivity according to Example 1 and another with a higher reinforcing ability according to Example 4 except that the coupling agent was 3-(triethoxysilyl)propylsuccinic anhydride and the surface modifier was 1-(triethoxysilyl)-2-(diethoxymethylsilyl) ethane (silane ratio 5:1). The reinforcing fibers were woven into a textile and the other chopped to 10 mm length.

The glass compositions were the following:
The glass having a higher bioactivity:

| | |
|---|---|
| $SiO_2$ | 59.7 weight-%, |
| $Na_2O$ | 25.5 weight-%, |
| CaO | 11.0 weight-%, |
| $P_2O_5$ | 2.5 weight-%, |
| $B_2O_3$ | 1.3 weight-%, |

The glass having higher reinforcing properties:

| | |
|---|---|
| $SiO_2$ | 65.5 weight-%, |
| $Na_2O$ | 12.0 weight-%, |
| CaO | 18.0 weight-%, |
| $P_2O_5$ | 1.5 weight-%, |
| $B_2O_3$ | 2.0 weight-%, |
| MgO | 1.0 weight-% |

The chopped fibers were fed into a 2 L rotary evaporator vessel and surface-treated with a 5 wt-% mixture of the coupling agent 3-(triethoxysilyl)propylsuccinic anhydride and a surface modifier 1-(triethoxysilyl)-2-(diethoxymethylsilyl) ethane (in a ratio of 5:1), in solution in 90 wt-% ethanol and 5 wt-% water, catalyzed with acetic acid (pH 4.5). After the reaction was complete, a solvent change was conducted to change the solvent to ethyl acetate and 1 wt-% PLLA compatibilizer (molecular weight of 2000 g/mol) was added together with a catalyst, 0.02 mol-% tin(II)-ethylhexanoate. After the reaction was complete, the matrix polymer PLDLA was added as a 10 wt-% solution in ethyl acetate. After full wetting of the fibers the textile was impregnated with the mixture and vacuum-treated. The composite was manufactured with compression molding into dimensions of 4×80×70 mm at a temperature of 190° C.

Example 10

Manufacturing Resorbable Reinforced Composite Plates

A variety of composite plates were manufactured according to the methods of Examples 1-9. The formulations used are shown in Table 1.

Example 11

Injection Moulding of Bioresorbable and Biocompatible Composite Screws, Rods and Bending Test Specimens The glass fibers were made according to the general procedure except the surface modification of cut fibers (5-10 mm) was carried out in a 2 L reaction vessel using 3-glycidoxyppropyltriethoxysilane treatment followed by addition of succinic acid-terminated PLLA compatibilizer (Mn 4000 g/mol) similar to Example 4, except that the process was a batch wise using a slurry process. Polymer matrix was combined with the surface modified cut fibers (20-40 wt-%) and dried under vacuum for 72 hours. PLLA, PLDLA and PLGA were used as polymer matrices in the manufacture of bioresorbable and biocompatible composite screws, rods and bending test specimens by injection moulding.

Typical injection moulding process included feeding of dried slurry pellets into a feeder hopper, using plastification temperature of 190-215° C., injection temperature of 180-205° C., nozzle temperature of 170-200° C. and mould temperature of 20-45° C. The processing conditions were suitable for producing uniform PLLA, PLDLA and PLGA based bioresorbable and biocompatible composite screws, rods and bending test specimens for further testing (as shown in Example 12 below).

Example 12

Flexural Properties of Bioresorbable and Biocompatible Glass Fibre Reinforced Composites Selected samples were manufactured according to Example 11 and a 3-point bending strength was measured according to ISO 178:2001 Plastics—Determination of flexural properties standard with Lloyd LRX Plus materials testing machine. The ISO standard used was that in force at the time of filing this application. Results of flexural properties testing are shown in Table 2.

TABLE 1

Manufacturing resorbable reinforced composite plates

| Glass fiber composition [wt-%] | Coupling agent | Surface modifier | Compatibilizer | (co)polymer matrix |
|---|---|---|---|---|
| $Na_2O$ 12%, CaO 18%, MgO 1%, $P_2O_5$ 1.5%, $B_2O_3$ 2%, $SiO_2$ 65.5% | 3-(triethoxysilyl)-propylsuccinic anhydride | n-propyl-triethoxysilane | PLLA 2000 g/mol | PLGA i.v. 2.3 |
| $Na_2O$ 12%, CaO 18%, MgO 1%, $P_2O_5$ 1.5%, $B_2O_3$ 2%, $SiO_2$ 65.5% | 3-glycidoxypropyl-triethoxysilane | octyl-triethoxysilane | PCL 8000 g/mol | PLLA/PCL i.v. 1.5 |
| $Na_2O$ 16%, CaO 18%, MgO 3.5%, $P_2O_5$ 1%, $SiO_2$ 61.5% | allyltriethoxysilane | n-propyl-triethoxysilane | Methacrylated PLLA 5000 g/mol | PLGA i.v. 2.3 |
| $Na_2O$ 10%, CaO 16%, MgO 6%, $P_2O_5$ 3%, $B_2O_3$ 1%, $SiO_2$ 64% | 3-glycidoxypropyl-triethoxysilane | 1-(triethoxysilyl)-2-(diethoxymethyl-silyl)ethane | PLLA 2000 g/mol | PLDLA i.v. 6.5 |
| $Na_2O$ 10%, CaO 22%, MgO 3%, $P_2O_5$ 3%, $B_2O_3$ 1%, $SiO_2$ 61% | 3-glycidoxypropyl-triethoxysilane | n-propyl-triethoxysilane | PLDLA 17000 g/mol | PLGA i.v. 2.3 |

PLLA = poly-L-lactide;
PCL = poly(ε-caprolactone);
PLDLA = L-lactide/DL-lactide copolymers;
PLGA = poly(lactide-co-glycolide);
i.v. = inherent viscosity

TABLE 2

Manufacturing resorbable reinforced composite plates

| Glass fiber composition [wt-%] | Fiber content [wt-%] | Fiber form | Coupling agent | Compatibilizer | (co)polymer matrix | Bending strength [MPa] | Bending Modulus [GPa] |
|---|---|---|---|---|---|---|---|
| $Na_2O$ 16%, CaO 14%, MgO 3.5%, $P_2O_5$ 1%, $B_2O_3$ 1.5%, $SiO_2$ 64% | 30 | Chopped | 3-glycidoxypropyl-triethoxysilane | Succinic acid terminated PLLA 2000 g/mol | PLGA i.v. 2.3 | 133 | 6.82 |
| $Na_2O$ 10%, CaO 16%, MgO 6%, $P_2O_5$ 3%, $B_2O_3$ 1%, $SiO_2$ 64% | 30 | Chopped | 3-glycidoxypropyl-triethoxysilane | Succinic acid terminated PLLA 2000 g/mol | PLDLA i.v. 3.8 | 144 | 9.0 |
| $Na_2O$ 10%, CaO 16%, MgO 6%, $P_2O_5$ 3%, $B_2O_3$ 1%, $SiO_2$ 64% | 30 | Continuous | 3-glycidoxypropyl-triethoxysilane | Succinic acid terminated PLLA 2000 g/mol | PLDLA i.v. 3.8 | 220 | 20.0 |
| $Na_2O$ 11%, CaO 18%, MgO 2.0%, $P_2O_5$ 0.5%, $B_2O_3$ 2.0%, $Al_2O_3$ 2.5%, $SiO_2$ 64% | 40 | Chopped | 3-glycidoxypropyl-triethoxysilane | Succinic acid terminated PLDLA | PLDLA i.v. 3.8 | 266 | 11.4 |

The invention claimed is:

1. A composite material comprising biocompatible and bioresorbable glass fibers embedded in a biocompatible and bioresorbable matrix polymer,
wherein said glass fibers are potassium free and comprise

| | | |
|---|---|---|
| $SiO_2$ | 60-70 | weight-%, |
| $Na_2O$ | 5-20 | weight-%, |
| CaO | 5-25 | weight-%, |
| MgO | 0-10 | weight-%, |
| $P_2O_5$ | 0.5-5 | weight-%, |
| $B_2O_3$ | 0-15 | weight-% and |
| $Al_2O_3$ | 0-5 | weight-%, | wherein a surface of said glass fibers has been reacted with an organosilane coupling agent,
wherein said coupling agent has been subsequently reacted with a compatibilizer,
wherein at least 10% of the structural units of the compatibilizer are identical to the structural units of the matrix polymer, and
wherein the molecular weight of the compatibilizer is less than 30000 g/mol.

2. The composite material of claim 1, wherein at least 30% of the structural units of the compatibilizer are identical to the structural units of the matrix polymer.

3. The composite material of claim 1, wherein the molecular weight of the compatibilizer is less than 10000 g/mol.

4. The composite material of claim 1, further comprising a surface modifier capable of protecting the glass fibers and to increase wetting of the glass fibers.

5. The composite material of claim 1, wherein the amount of the biocompatible and bioresorbable glass fibers is 1-90 weight-% of the total weight of the composite material.

6. The composite material of claim 1, wherein the amount of matrix polymer is 1-90 weight-% of the total weight of the composite material.

7. The composite material of claim 1, wherein the amount of coupling agent is 0.1-10 weight-% of the amount of glass.

8. The composite material of claim 1, wherein the amount of compatibilizer is 0.1-20 weight-% of the total weight of the composite material.

9. The composite material of claim 1, wherein the matrix polymer and the compatibilizer are independently selected from the group consisting of polylactides (PLA), poly-L-lactide (PLLA), poly-DL-lactide (PDLLA), polyglycolide (PGA), copolymers of glycolide, glycolide/trimethylene carbonate copolymers (PGA/TMC), lactide/tetramethylglycolide copolymers, lactide/trimethylene carbonate copolymers, lactide/d-valerolactone copolymers, lactide/ε-caprolactone copolymers, L-lactide/DL-lactide copolymers (PLDLA), glycolide/L-lactide copolymers (PGA/PLLA), polylactide-co-glycolide, lactide/glycolide/trimethylene carbonate terpolymers, lactide/glycolide/ε-caprolactone terpolymers, PLA/polyethylene oxide copolymers, polydepsipeptides, unsymmetrically 3,6-substituted poly-1,4-dioxane-2,5-diones, polyhydroxybutyrates (PHB), PHB/b-hydroxyvalerate copolymers (PHB/PHV), poly-b-hydroxypropionate (PHPA), poly-p-dioxanone (PDS), poly-d-valerolactone-poly-ε-caprolactone, poly(ε-caprolactone-DL-lactide) copolymers, methylmethacrylate-N-vinyl pyrrolidone copolymers, polyesteramides, polyesters of oxalic acid, polydihydropyrans, polyalkyl-2-cyanoacrylates, polyurethanes (PU), polyvinylalcohol (PVA), polypeptides, poly-b-malic acid (PMLA), poly-b-alkanoic acids, polycarbonates, polyorthoesters, polyphosphates, poly(ester anhydrides), and mixtures thereof.

10. The composite material of claim 1, further comprising an organosilane surface modifier for said glass fibers.

11. The composite material of claim 1, wherein the coupling agent is selected from the group of alkyoxy silanes.

12. The composite material of claim 10, wherein the surface modifier is selected from the group consisting of alkyl-silanes.

13. The composite material of claim 1, wherein it comprises at least one biocompatible and bioresorbable glass fiber and at least one bioactive, biocompatible and bioresorbable glass fiber, the glass fibers having different compositions.

14. The composite material of claim 1, wherein it comprises at least one biologically active compound selected from the group consisting of bioactive glass, hydroxyl apatite and tricalciumphosphate.

15. A medical device comprising the composite material of claim 1.

16. The medical device of claim 15, in the form of an implant.

17. Process for manufacturing the composite material of claim 1, comprising the steps of
  treating a surface of the glass fibers by extraction with de-ionized water in order to remove ions from said surface,
  reacting a coupling agent with a surface of the glass fibers to produce treated glass fibers,
  reacting a compatibilizer with the coupling agent of the treated glass fibers, and
  adding the polymer matrix material to the glass fibers to produce the composite material.

* * * * *